United States Patent [19]

Blattner et al.

[11] 4,263,315
[45] Apr. 21, 1981

[54] AZATETRACYCLIC CARBONITRILES

[75] Inventors: Hans Blattner, Riehen; Angelo Storni, Rheinfelden, both of Switzerland

[73] Assignee: Ciba-Geigy Corporation, Ardsley, N.Y.

[21] Appl. No.: 54,318

[22] Filed: Jul. 2, 1979

[30] Foreign Application Priority Data

Jul. 7, 1978 [CH] Switzerland ............ 7420/78

[51] Int. Cl.³ ............ H61K 31/55; C07D 487/06; C07D 491/06
[52] U.S. Cl. ............ 424/274; 260/245.7; 260/326.27; 260/326.28; 260/326.29; 260/326.31; 260/326.5 B; 260/326.5 SA; 260/326.62
[58] Field of Search ............ 260/245.7, 326.62, 326.27, 260/326.28, 326.29, 326.31, 326.5 B, 326.5 SA; 424/274

[56] References Cited

U.S. PATENT DOCUMENTS

| | | | |
|---|---|---|---|
| 3,636,045 | 1/1972 | Blattner et al. | 260/326.5 SA |
| 3,636,046 | 1/1972 | Blattner et al. | 260/326.5 B |
| 3,726,897 | 4/1973 | Schindler | 260/326.27 |
| 3,755,357 | 8/1973 | Schindler et al. | 260/326.5 B |
| 4,076,830 | 2/1978 | Ciganek | 260/326.62 |
| 4,112,110 | 9/1978 | Blattner | 260/326.5 SA |
| 4,145,434 | 3/1979 | Van der Burg | 260/326.5 SA |
| 4,158,058 | 6/1979 | Van der Burg | 260/326.5 SA |

FOREIGN PATENT DOCUMENTS 550788 of 1974 Switzerland ............ 260/326.27

Primary Examiner—Mary C. Lee
Attorney, Agent, or Firm—Prabodh I. Almaula

[57] ABSTRACT

Azatetracyclic carbonitriles of the formula I

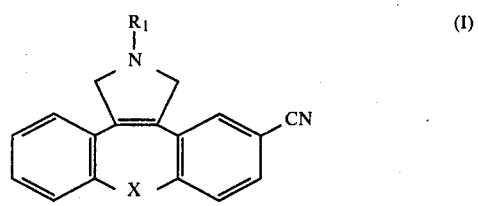

in which $R_1$ is hydrogen, lower alkyl, cycloalkyl-lower alkyl, lower alkenyl or free, etherified or esterified hydroxy-lower alkyl, and X is epoxy, epithio, methylene of a divalent radical of the partial formula

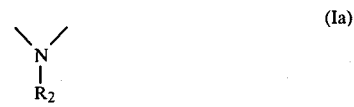

in which $R_2$ is hydrogen or lower alkyl, and salts of such compounds, their preparation, pharmaceutical preparations which contain these compounds and the use thereof.

15 Claims, No Drawings

AZATETRACYCLIC CARBONITRILES

The invention relates to novel azatetracyclic carbonitriles, especially 5-cyano-2,3-dihydro-1H-dibenzo[2,3:6,7]thiepino[4,5-c]pyrroles substituted in the 2-position and corresponding oxepino, azepino and cycloheptatrieno compounds, and the salts of such compounds, processes for their preparation, pharmaceutical compositions which contain the novel compounds, and the use thereof.

The azatetracyclic carbonitriles according to the invention have the formula I

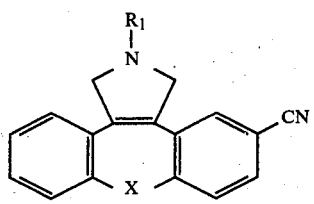

(I)

in which $R_1$ is hydrogen, lower alkyl, cycloalkyl-lower alkyl, lower alkenyl or free, etherified or esterified hydroxy-lower alkyl and X is epoxy, epithio, methylene or a divalent radical of the partial formula

(Ia)

in which $R_2$ is hydrogen or lower alkyl.

Lower alkyl $R_1$ preferably contains 1 to 7 carbon atoms. These lower alkyl groups, which can be straight-chain or branched, are, for example, methyl, ethyl, propyl, isopropyl, butyl, isobutyl or tertiary butyl.

A cycloalkyl-lower alkyl radical $R_1$ preferably contains 4 to 8 carbon atoms. Cycloalkyl-lower alkyl is thus, for example, cyclopropylmethyl, cyclobutylmethyl and especially cyclopentylmethyl or cyclohexylmethyl and also, for example, cyclopropylethyl, cyclobutylethyl, cyclopentylethyl or cyclohexylethyl.

A lower alkenyl radical $R_1$ preferably contains 3 to 4 carbon atoms and especially 3 carbon atoms. Lower alkenyl is, for example, in the form of allyl or 2-methylallyl.

Substituents of lower alkyl are free, etherified or esterified hydroxyl. Such radicals are, for example, hydroxy-lower alkyl, lower alkoxy-lower alkyl or alkanoyloxy-lower alkyl.

In a hydroxy-lower alkyl radical $R_1$, the hydroxyl group is separated from the ring nitrogen atom by at least 2 carbon atoms. This radical contains 2 to 8 and preferably 2 to 4 carbon atoms. Hydroxy-lower alkyl, which can be straight-chained or branched, is, for example, 1-methyl-2-hydroxyethyl, 2-hydroxypropyl, 1- or 2-methyl-2-hydroxypropyl and especially 2-hydroxyethyl and 3-hydroxypropyl.

In a lower alkoxy-lower alkyl radical $R_1$, the oxygen atom is separated from the ring nitrogen atom by at least 2 carbon atoms. This radical contains, for example, 3 to 10 and preferably 3 to 6 carbon atoms. This lower alkoxy-lower alkyl is, for example, 2-methoxypropyl, 2- or 3-ethoxypropyl, 2- or 3-propoxypropyl, 3-isopropoxypropyl and especially 2-methoxy- or 2-ethoxyethyl and in particular 3-methoxypropyl.

In an alkanoyloxy-lower alkyl radical $R_1$, the oxygen atom is separated from the ring nitrogen atom by at least 2 carbon atoms. This radical contains, for example, 3 to 21 and preferably 4 to 11 carbon atoms. This radical is, for example, 2-formyloxy-ethyl, 2acetyloxy-ethyl, 2-propionyloxy-ethyl, 2-acetyloxy-propyl, 2-methyl-3-acetyloxy-propyl or 2- or 3-propionyloxy-propyl and especially 3-acetyloxypropyl and 3-octanoyloxypropyl.

$R_2$ is preferably hydrogen or lower alkyl having not more than 4 carbon atoms, such as propyl, butyl, isobutyl and in particular methyl or ethyl.

Salts of compounds of the formula I are acid addition salts, especially pharmaceutically acceptable acid addition salts, for example with inorganic acids, such as hydrochloric acid, hydrobromic acid, sulfuric acid or phosphoric acid, or with organic acids, such as organic carboxylic and sulfonic acids, such as methanesulfonic acid, ethanesulfonic acid, 2-hydroxyethanesulfonic acid, acetic acid, malic acid, tartaric acid, citric acid, lactic acid, oxalic acid, succinic acid, fumaric acid, maleic acid, benzoic acid, salicylic acid, phenylacetic acid, mandelic acid or embonic acid.

The novel azatetracyclic carbonitriles of the general formula I and their acid addition salts have valuable pharmacological properties, for example they act on the central nervous system. They are distinguished in particular by long-lasting sedative actions on the central nervous system and stimulation-inhibiting (amphetamine-antagonistic) actions, as can be demonstrated with the aid of pharmacological tests. Thus, in rats, in the amphetamine antagonism test (Nemegeers and Janssen, Arzneimittelforsch., volume 24, page 45 (1974)) they display a stimulation-inhibiting action in a dosage range of 0.01 to 1.0 mg/kg administered intraperitoneally or perorally. The novel azatetracyclic carbonitriles of the general formula I and their pharmaceutically acceptable acid addition salts can therefore be used as tranquillising, antipsychotic and stimulation-inhibiting compounds for the treatment of states of agitation.

The invention relates in particular to compounds of the formula I in which $R_1$ is hydrogen, lower alkyl, for example methyl, ethyl, isopropyl and n-butyl, cycloalkyl-lower alkyl having 4–8 carbon atoms, for example cyclopentylmethyl and cyclohexylmethyl, lower alkenyl, for example allyl, hydroxy-lower alkyl, for example 2-hydroxyethyl and 3-hydroxypropyl, lower alkoxy-lower alkyl, for example 3-methoxy- and 3-ethoxy-propyl, or alkanoyloxy-lower alkyl, for example 3-acetyloxy-propyl and 3-octanoyloxy-propyl, and X is epoxy, epithio, methylene or the divalent radical of the partial formula Ia

(Ia)

in which $R_2$ is hydrogen or lower alkyl having not more than 4 carbon atoms, preferably methyl or ethyl, and salts thereof, especially acid addition salts and in particular pharmaceutically acceptable acid addition salts thereof.

The invention relates especially to compounds of the formula I in which $R_1$ is hydrogen, lower alkyl, for example methyl, ethyl or propyl, cycloalkyl-lower alkyl having 4–8 carbon atoms, for example cyclopentylmethyl and cyclohexylmethyl, lower alkenyl, for example allyl, or hydroxy-lower alkyl, for example 2-hydroxyethyl and 3-hydroxypropyl, and X is epoxy or epithio, and salts thereof, especially acid addition salts and in particular pharmaceutically acceptable acid addition salts thereof.

The invention relates in particular to compounds of the formula I in which $R_1$ is hydrogen, methyl, ethyl, propyl, cyclopentylmethyl or 3-hydroxypropyl and X is epoxy or epithio, such as 2-methyl-5-cyano-2,3-dihydro-1H-dibenzo[2,3:6,7]thiepino[4,5-c]pyrrole, 2-ethyl-5-cyano-2,3-dihydro-1H-dibenzo[2,3:6,7]thiepino[4,5-c]pyrrole, 2-(cyclopentylmethyl)-5-cyano-2,3-dihydro-1H-dibenzo[2,3:6,7]thiepino[4,5-c]pyrrole, 2-propyl-5-cyano-2,3-dihydro-1H-dibenzo[2,3:6,7]thiepino[4,5-c]pyrrole, 5-cyano-2,3-dihydro-1H-dibenzo[2,3:6,7]-thiepino[4,5-c]pyrrole-3propanol or 2-ethyl-5-cyano-2,3-dihydro-1H-dibenz[2,3:6,7]oxepino[4,5-c]pyrrole, and salts thereof, especially acid addition salts and in particular pharmaceutically acceptable acid addition salts thereof.

The compounds of the formula I are prepared in a manner known per se. Thus, they are obtained, for example, by reacting a reactive diester of a dimethanol of the formula

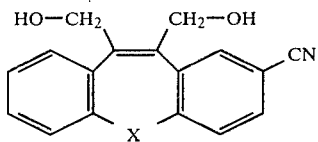

with a compound of the formula

Reactive diesters of a dimethanol of the formula II which can be used are esters with strong inorganic acids, for example hydrochloric and hydroiodic acids or especially hydrobromic acid. Furthermore, corresponding diesters of strong organic acids, for example of sulfonic acids, such as methanesulfonic acid, benzenesulfonic acid, p-chloro- or p-bromo-benzenesulfonic acid or p-toluenesulfonic acid, can also be used. These diesters of the compounds of the formula II are preferably reacted in a suitable inert solvent at a reaction temperature of 20° to 130° C. Suitable inert solvents are, for example, hydrocarbons, such as benzene or toluene, halogenated hydrocarbons, such as chloroform, lower alcohols, such as ethanol and especially methanol, ether-like liquids, such as ether or dioxan, and lower alkanones, for example acetone, methyl ethyl ketone or diethyl ketone, or mixtures of such solvents, for example benzene/methanol.

When one mol equivalent of a diester of a dimethanol of the formula II is reacted with one mol equivalent of a free base of the formula III, two mol equivalents of an acid are eliminated and these are preferably bound with an acid-binding agent. Examples of suitable acid-binding agents are alkali metal carbonates, such as potassium carbonate, or, for example alkali metal hydroxides, such as sodium hydroxide or potassium hydroxide, or excess base of the formula III, and also tertiary organic bases, such as pyridine and especially triethylamine or N-ethyl-diisopropylamine.

The direct starting materials, i.e. the reactive diesters of dimethanols of the formula II, can be prepared in a manner known per se, for example from the corresponding dimethyl compounds by bromination, for example with N-bromosuccinimide.

According to a further process, the compounds of the formula I are obtained by reacting a compound of the formula

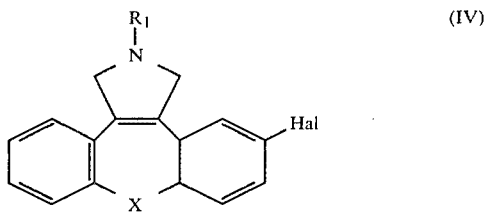

in which Hal is a halogen atom, with a cyanide compound.

Chlorine or iodine, but preferably bromine, are chosen as the Hal radicals in compounds of the formula IV. Cyanide compounds are in particular alkali metal cyanides or heavy metal cyanides. The preferred alkali metal cyanide is sodium cyanide. However, copper-I cyanide, as a representative of the heavy metal cyanides, is very particularly suitable. The reaction can be carried out in the presence or absence of solvents and in a temperature range of 80° to 250°. Suitable solvents are especially pyridine, quinoline, dimethylformamide, 1-methyl-2-pyrrolidinone and hexamethylphosphoric acid triamide. The two last-mentioned solvents are particularly suitable when copper-I cyanide is used as the cyanating agent.

The starting materials of the formula IV are known or can be prepared by methods known per se, for example analogously to the first-mentioned process. In this context reference should be made, inter alia, to German Offenlegungsschriften Nos. 1,959,405, 1,965,969 and 2,125,634.

If desired, a compound of the formula I in which the radical $R_1$ is hydrogen can be converted to a process product in which the radical $R_1$ has one of the other meanings defined.

Thus, for example, a N-substitution can be effected, either by treatment with a reactive ester of a corresponding alcohol of the formula $R_1'$-OH, in which $R_1'$ has the meanings defined for $R_1$ in formula I with the exception of hydrogen, or by a reaction with a corresponding aldehyde or ketone under reducing conditions.

The reaction of compounds of the formula I in which $R_1$ is hydrogen with a reactive ester of a hydroxy compound of the formula $R_1'$-OH is preferably carried out in a solvent at a reaction temperature of 20° to 130° C., especially at the boiling point of the solvent, and, if desired, in the presence of an acid-binding agent.

Examples of reactive esters which can be used are halides, such as chlorides or bromides, and also sulfonates, such as the p-toluenesulfonate, or sulfuric acid esters. Suitable acid-binding agents are alkali metal carbonates, for example potassium carbonate, or alkali metal hydroxides, for example sodium hydroxide, or tertiary organic bases, for example pyridine or N-ethyldiisopropylamine. Suitable solvents are those solvents which are inert under the reaction conditions, for example hydrocarbons, such as benzene or toluene, and also alkanols, for example methanol or ethanol, or alkanones, such as acetone or methyl ethyl ketone.

Aldehydes and ketones which correspond to the alcohols of the formula $R_1'$-OH are, for example, lower aliphatic aldehydes or ketones and also lower, free, esterified or etherified hydroxyoxoalkanes. The reaction product obtained from the reaction of these aldehydes or ketones with the said compounds of the formula I can be reduced in the same operation or subsequently.

The aldehydes, for example formaldehyde or acetaldehyde, or the ketones, for example acetone, are, for example, warmed with the said compounds of the formula I in an inert solvent to about 30° to 100° C. and, at the same time or subsequently, the reaction mixture is hydrogenated with hydrogen in the presence of a catalyst. Suitable solvents are, for example, alkanols, such as methanol or ethanol, and suitable catalysts are noble metal catalysts, such as palladium-on-charcoal.

However, other reducing agents, for example formic acid, can also be used, in place of hydrogen in the presence of a catalyst, for the reductive alkylation. According to this variant of the process, the said compounds of the formula I are warmed with formic acid and the said types of aldehydes or ketones, especially formaldehyde, preferably in excess, without a further solvent.

Furthermore, if desired, a compound of the formula I in which the radical $R_1$ is a hydroxy-lower alkyl group can be acylated to a compound in which the radical $R_1$ is an esterified hydroxy-lower alkyl group.

The acylation can be carried out, for example, with a carboxylic acid anhydride, including a corresponding carboxylic acid halide, at a reaction temperature between about 20° and 100° C. Since the condensation reaction proceeds with the elimination of acid, it is preferable to add an acid-binding agent, for example a tertiary organic base, such as pyridine, to the reaction mixture. Excess tertiary organic base can also be used as the solvent. Furthermore, hydrocarbons, for example benzene or toluene, or halogenated hydrocarbons, for example chloroform, can be used as solvents.

Furthermore, if desired, a resulting process product of the general formula I in which the radical $R_1$ is a free hydroxy-lower alkyl group is etherified to a reaction product in which the radical $R_1$ is an etherified lower hydroxyalkyl group.

The etherification can be effected by reacting the hydroxyalkyl compound, preferably in a solvent, in the presence of a condensing agent with a reactive ester of an alcohol. Suitable reactive esters are, for example, esters of hydrogen halide acids, for example of hydrobromic acid or hydroiodic acid, or sulfonic acid esters, for example p-toluenesulfonate. Condensing agents which can be used are, for example, alkali metal alkanolates, for example sodium methylate or sodium ethylate, or alkali metal hydrides, for example sodium hydride, or metal amides, such as sodium amide or lithium amide. Suitable solvents are inert solvents, for example hydrocarbons, such as benzene or toluene, or, if alkanolates are used as the condensing agent, corresponding alkanols. The reaction temperatures are preferably between 20° and 130° C.

Furthermore, if desired, a compound of the formula I in which X is a divalent radical of the partial formula

(Ia)

and in which $R_2$ is hydrogen can be converted to another process product in which the radical $R_2$ is lower alkyl.

This conversion is preferably effected by reacting the abovementioned process product in the presence of solvents and basic condensing agents with a reactive lower alkyl ester.

Reactive esters which can be used are, for example, lower alkyl halides, such as lower alkyl chlorides or bromides, and also sulfonic acid esters, such as methyl p-toluenesulfonate or ethyl p-toluenesulfonate, or sulfuric acid esters, for example dimethyl sulfate or diethyl sulfate. Suitable basic condensing agents are alkali metal alkanolates, such as potassium tert.-butylate or corresponding amides, such as sodium amide, or metal hydrides, such as sodium hydride or lithium hydride. Suitable solvents are those solvents which are inert under the reaction conditions, for example hydrocarbons, such as benzene or toluene, and also ether-like solvents, for example tetrahydrofuran, dioxan or ethylene glycol dimethyl ether, or amides, such as phosphoric acid hexamethyltriamide or dimethylformamide.

Depending on the process conditions and the starting materials, the end products may be obtained in the free form or in the form of their salts, and these can be converted into one another or into other salts in a conventional manner. Thus, free compounds of the formula I can be formed from resulting acid addition salts, for example by treatment with bases or basic ion exchangers, whilst free bases of the formula I can be converted to acid addition salts, for example by reaction with organic or inorganic acids, especially those which are suitable for forming pharmaceutically usable salts, such as those mentioned above.

Salts of the novel compounds can also be used for the purposes of purification, for example by converting the free compounds to their salts, isolating and, if necessary, purifying the salts and converting them into the free compounds again. Because of the close relationship between the novel compounds in the free form and in the form of their salts, what is stated in this specification in respect of the free compounds also applies by analogy to the corresponding salts.

The invention also relates to those embodiments of the process in which a compound obtainable as an intermediate at any stage of the process is used as the starting material and the missing process steps are carried out, or the process is discontinued at any stage, or in which a starting material is formed under the reaction conditions, or in which a reactant may be in the form of its salts.

The starting materials used for carrying out the process according to the invention are preferably those which result in the groups of end products mentioned in particular initially and particularly in the end products which have been specifically described or singled out.

The novel compounds can be used, for example, in the form of pharmaceutical preparations which contain an effective amount of the active substance, if desired together with inorganic or organic, solid or liquid, pharmaceutically usable carriers which are suitable for enteral, for example oral, or parenteral administration. Thus, tablets or gelatin capsules are used which contain the active ingredient together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, corn starch, rice starch or arrowroot, gelatin, tragacanth, methylcellulose, sodium carboxymethylcellulose and/or polyvinylpyrrolidone, and, if desired, disintegrators, for example starches, agar or alginic acid or a salt thereof, such as sodium alginate, and/or effervescent mixtures, or adsorbents, dyes, flavourings and sweeteners. Furthermore, the novel pharmacologically active compounds can be used in the form of injectable preparations, for example preparations which can be administered intravenously, or of infusion solutions. Such solutions are preferably isotonic aqueous solutions or suspensions, and these can be prepared before use, for example in the form of lyophilised preparations which contain the active ingredient on its own or together with a carrier, for example mannitol. The pharmaceutical preparations can be sterilised and/or contain adjuncts, for example preservatives, stabilisers, wetting agents and/or emulsifiers, solubilising agents, salts for regulating the osmotic pressure and/or buffers. The pharmaceutical preparations of this specification which, if desired, can contain further pharmacologically valuable substances, are prepared in a manner known per se, for example by means of conventional mixing, granulating, sugar-coating, dissolving or lyophilising methods, and contain from about 0.1 to 100% and in particular from about 1% to about 50% of the active ingredient; lyophilisates contain up to 100% of the active ingredient. The dosage depends on the mode of administration, the species and the age and on the individual condition. The daily doses of the free bases or of pharmaceutically acceptable salts thereof vary between about 0.01 mg/kg and 1 mg/kg for warm-blooded animals in general and between about 0.001 g to about 0.025 g for warm-blooded animals weighing about 70 kg.

The following examples serve to illustrate the invention; temperatures are in degrees Centigrade.

EXAMPLE 1

42.1 g (0.1 mol) of 2-cyano-10,11-bis-bromomethyl-dibenzo[b,f]thiepine are dissolved in 250 ml of absolute benzene and the solution is added dropwise in the course of one hour, at 40°, to a solution of 62 g (2 mols) of methylamine in 500 ml of methanol. The reaction mixture is stirred for a further two hours at 50° and the solvent and the excess methylamine are then distilled off. Water is added to the residue and the resulting suspension is extracted with ether. The organic phase is separated off, washed with water, dried over potassium carbonate and concentrated. On cooling, 2-methyl-5-cyano-2,3-dihydro-1H-dibenzo[2,3:6,7]thiepino[4,5-c]pyrrole with a melting point of 132°–136° crystallises out.

14.5 g (0.05 mol) of the resulting base are dissolved in 200 ml of acetone and 4.8 g (0.05 mol) of methanesulfonic acid are then added carefully, whereupon the methanesulfonate crystallises out; after recrystallisation from absolute ethanol, this melts at 263°–266°.

The starting material can be prepared as follows:

4.3 g of sodium amide (in the form of a 2% suspension in toluene) are added in the course of 30 minutes to a solution of 30.5 g of 8-bromo-10,11-dihydro-dibenz[b,f]-thiepin-10-one in 200 ml of absolute benzene. The mixture is then refluxed for two hours and cooled to 50° and 19.9 g of methyl iodide are added dropwise. The suspension is then stirred for 20 hours at 50° and cooled and 200 ml of water are added. The organic phase is separated off, washed with 50 ml of water, dried over sodium sulfate and evaporated to dryness under reduced pressure. The residue is crystallised at room temperature from 70 ml of absolute ether. The 8-bromo-11-methyl-10,11-dihydro-dibenz[b,f]thiepin-10-one melts at 124°–126°.

A solution of 11.5 g of 8-bromo-11-methyl-10,11-dihydro-dibenz[b,f]thiepin-10-one in 50 ml of absolute benzene is added, at 0°, to a Grignard solution, which has been prepared by adding 10.2 g of methyl iodide to 1.76 g of magnesium in 17.5 ml of absolute ether, whilst passing nitrogen through the Grignard solution. The mixture is then stirred for 16 hours and poured into 200 ml of ice-water. The oil which has separated out is dissolved in 100 ml of ether and the ether solution is washed with 20 ml of water, dried over magnesium sulfate and concentrated under reduced pressure. After adding a little petroleum ether, 2-bromo-10,11-dimethyl-11-hydro-10,11-dihydro-dibenz[b,f]thiepine is obtained in the form of colourless crystals; melting point 96°–98°.

A suspension of 7.7 g of 2-bromo-10,11-dimethyl-11-hydroxy-10,11-dihydro-dibenz[b,f]thiepine in 40 ml of 20% sulfuric acid is refluxed for 36 hours, with rapid stirring. The mixture is then cooled and extracted with three times 50 ml of ether. The ether extracts are combined, washed with water until neutral, dried over magnesium sulfate and evaporated to dryness under reduced pressure. The residue is dissolved in 32 ml of 20% ethanolic potassium hydroxide solution and the solution is refluxed for 40 hours. It is then concentrated to dryness under reduced pressure and the residue is extracted with 100 ml of ether. The ether solution is washed with 20 ml of water, dried over magnesium sulfate and evaporated to dryness under reduced pressure. The residue is dissolved in 300 ml of methanol, a small amount of insoluble matter is filtered off and the filtrate is concentrated under reduced pressure. 2-Bromo-10,11-dimethyl-dibenz[b,f]thiepine is obtained in the form of yellowish crystals; melting point 108°–111°.

31.7 g (0.1 mol) of 2-bromo-10,11-dimethyldibenzo[b,f]thiepine, 10.7 g (0.12 mol) of copper-I cyanide and 15 ml of dimethylformamide are heated at a bath temperature of 200° for 3 hours, with stirring. The reaction mixture is then cooled to 40° and stirred vigorously for 2 hours with 200 ml of a 50% aqueous solution of ethylenediamine and 200 ml of methylene chloride. The organic phase is then separated off and the aqueous phase is extracted twice more with 100 ml of methylene chloride. The combined organic solutions are washed with water, dried over sodium sulfate and evaporated. The residue, i.e. 2-cyano-10,11-dimethyl-dibenz[b,f]-thiepine, is recrystallised from methanol and melts at 134°–135°.

26.3 g (0.1 mol) of 2-cyano-10,11-dimethyl-dibenzo[b,f]thiepine are dissolved in 525 ml of carbon tetrachloride and 35.6 g (0.2 mol) of N-bromosuccinimide are added to this solution. Whilst stirring in a nitrogen atmosphere, the mixture is heated to the boil under exposure to a UV lamp. The mixture is kept at the boil until all the N-bromosuccinimide, which is on the base of the vessel, has been converted to succinimide floating on the solution; time taken about 10 minutes. The reaction mixture is then cooled to 20° and the succinimide is separated off by filtration. The filtrate is washed with water, dried over sodium sulfate and concentrated in vacuo. On cooling, 2-cyano-10,11-bis-bromomethyl-dibenzo[b,f]thiepine with a melting point of 165°–167° crystallises out.

EXAMPLE 2

The following compounds can be prepared analogously to Example 1, using the corresponding starting materials:

(a) 2-Ethyl-5-cyano-2,3-dihydro-1H-dibenzo[2,3:6,7]-thiepino[4,5-c]pyrrole, melting point 129°–131° (from acetonitrile); methanesulfonate melting point 258°–260° (from absolute ethanol), from 42.1 g (0.1 mol) of 2-cyano-10,11-bis-bromomethyl-dibenzo[b,f]-thiepine and 90 g (2 mols) of ethylamine in 500 ml of methanol;

(b) 2-(Cyclopentylmethyl)-5-cyano-2,3-dihydro-1H-dibenzo[2,3:6,7]thiepino[4,5-c]pyrrole, melting point 97°–100° (from acetonitrile); methanesulfonate melting point 162°–168° (from absolute ethanol), from 42.1 g (0.1 mol) of 2-cyano-10,11-bis-bromomethyl-dibenzo[b,f]thiepine and 49.5 g (0.5 mol) of (aminomethyl)-cyclopentane in 300 ml of methanol;

(c) 2-Propyl-5-cyano-2,3-dihydro-1H-dibenzo[2,3:6,7]-thiepino[4,5-c]pyrrole, melting point 130°–131° (from diethyl ether); methanesulfonate melting point 135°–137° (from absolute ethanol/absolute diethyl ether), from 42.1 g (0.1 mol) of 2-cyano-10,11-bis-bromomethyl-dibenzo[b,f]thiepine and 59 g (1 mol) of propylamine in 250 ml of methanol; and (d) 5-Cyano-1,3-dihydro-2H-dibenzo[2,3:6,7]-thiepino[4,5-c]pyrrole-2-propanol, crude product; hydrochloride melting point 273°–276° (from methanol), from 42.1 g (0.1 mol) of 2-cyano-10,11-bis-bromomethyl-dibenzo[b,f]thiepine and 37.5 g (0.5 mol) of 3-aminopropanol in 250 ml of methanol.

EXAMPLE 3

The following compound can be prepared analogously to Example 1 using the corresponding starting materials:

2-Ethyl-5-cyano-2,3-dihydro-1H-dibenz[2,3:6,7]ox-epino[4,5-c]pyrrole, melting point 125°–127° (from diethyl ether); methanesulfonate melting point 199°–201° (from absolute ethanol/acetone), from 40.5 g (0.1 mol) of 2-cyano-10,11-bis-bromomethyl-dibenz[b,f]oxepine and 90 g (2 mols) of ethylamine in 500 ml of methanol.

The starting material can be prepared as follows:

A mixture of 560.0 g of 2-(4-bromo-phenoxy)benzoic acid in 1,940 ml of absolute benzene, 218 ml of absolute ethanol and 32.6 ml of concentrated sulfuric acid is refluxed for 32 hours, the water formed being removed in a water separator. The reaction mixture is cooled to 10° and washed, with the addition of ice, with 1,000 ml of water, 500 ml of a 2 N aqueous sodium carbonate solution and then again with 1,000 ml of water. The organic phase is separated off, dried over magnesium sulfate and evaporated at 40° under a pressure of 11 mm Hg. The residue is distilled under a high vacuum and yields ethyl 2-(4-bromo-phenoxy)-benzoate, boiling point 140°–150°/0.05 mm Hg.

A solution of 477.0 g of ethyl 2-(4-bromo-phenoxy)-benzoate in 900 ml of absolute diethyl ether is added dropwise in the course of 1 hour to 42.3 g of lithium aluminium hydride in 500 ml of diethyl ether, whilst passing a stream of nitrogen through the mixture. The reaction mixture is refluxed for 6 hours and cooled to 0°–5° and, whilst passing nitrogen through the mixture, 450 ml of ethyl acetate and then, with care, 350 ml of water are added. The precipitate is filtered off and washed with diethyl ether. The aqueous phase of the filtrate is separated off and washed with 100 ml of diethyl ether; the combined organic phases are dried over magnesium sulfate and evaporated to dryness under 11 mm Hg; the residue is 2-(4-bromo-phenoxy)-benzyl alcohol in the form of a colourless oil.

A mixture of 413.0 g of 2-(bromo-phenoxy)-benzyl alcohol and 1,290 ml of 48% hydrobromic acid is refluxed for 4 hours and then cooled and poured onto 2,000 ml of ice and water. The greenish oil which has separated out is dissolved in 2,000 ml of diethyl ether. The organic phase is washed twice with 400 ml of water and with 400 ml of a 1 N aqueous solution of sodium bicarbonate, dried over magnesium sulfate and evaporated at 40° under 11 mm Hg. The 2-(4-bromophenoxy)-benzyl bromide which is obtained as an oily residue is used further without purification.

457.8 g of the crude 2-(4-bromo-phenoxy)-benzyl bromide are added in the course of one hour to a mixture, which is boiling under reflux, of 171.0 g of sodium cyanide in 160 ml of water and 44 ml of ethanol; 362 ml of ethanol are added dropwise at the same time. The mixture is then refluxed for a further 3 hours and is then diluted with 1,500 ml of water. The aqueous/ethanolic phase is washed with 1,000 ml of diethyl ether and the ether phase is separated off, washed twice with 200 ml of water, dried over magnesium sulfate and concentrated to dryness under 11 mm Hg. The residue is crystallised from a mixture of diethyl ether and petroleum ether and 2-(4-bromophenoxy)-phenylacetonitrile with a melting point of 56°–58° is thus obtained.

25.3 g of sodium are dissolved in 400 ml of absolute ethanol, with stirring, and about 200 ml of absolute ethanol are then distilled off from the reaction mixture again. 1,500 ml of absolute toluene are then added and distillation under a Vigreux column is continued until the boiling point is 108°, sodium ethylate crystallising out. At 100°–110°, a mixture of 288 g (1 mol) of 2-(4-bromophenoxy)-phenylacetonitrile and 354 g (3 mols) of diethyl carbonate is now added dropwise in the course of one hour, the ethanol formed being distilled off at the same time. After the dropwise addition is complete, the reaction mixture is further distilled until the boiling point is again 108°–110°. The reaction mixture is then cooled to room temperature and diluted with 300 ml of absolute toluene and 170 g (1.2 mols) of methyl iodide are added dropwise in the course of one hour. In order to bring the reaction to completion, the mixture is stirred for a further 1 hour at room temperature and for 5 hours at 80°. After cooling to room temperature, 1 liter of water is allowed to run in and the organic phase is separated off, washed with water and, after drying over sodium sulfate, completely evaporated in vacuo. Crude ethyl 2-(4-bromophenoxy)-phenyl-α-methyl-cyanoacetate remains as the residue.

374 g (1 mol) of crude ethyl 2-(4-bromophenoxy)-phenyl-α-methyl-cyanoacetate, 830 ml of 96% ethanol and 460 ml of 50% aqueous potassium hydroxide solution are refluxed for 24 hours, with good stirring. The reaction mixture is then evaporated at 50° under 11 mm Hg and the residue is dissolved in 3,500 ml of water.

After filtering to obtain a clear filtrate, the alkaline solution is acidified with concentrated hydrochloric acid, whereupon 2-(4-bromophenoxy)-phenyl-α-methylacetic acid crystallises out. After filtering off, the resulting acid is dried in vacuo at 50° and is then recrystallised from acetonitrile; melting point 99°–101°.

321 g (1 mol) of 2-(4-bromophenoxy)-phenyl-α-methylacetic acid and 3,210 g of polyphosphoric acid are warmed at 100°–105° for one hour, with good stirring. The reaction mixture is then poured into 3 liters of water, with stirring, the temperature being kept below 10° by adding ice. The oil which has separated out is extracted with diethyl ether and the organic phase is washed with water, dried over potassium carbonate and concentrated and, after cooling, 8-bromo-11-methyl-dibenz[b,f]oxepin-10-(11H)-one with a melting point of 85°–87° crystallises out.

A solution of 303 g (1 mol) of 8-bromo-11-methyl-dibenz[b,f]oxepin-10(11H)-one in 1,500 ml of absolute toluene is allowed to run dropwise, in the course of 5 hours, with good stirring, into a Grignard solution, which is prepared from 49 g (2 mols) of magnesium, 450 ml of absolute ether and 284 g of methyl iodide, a reaction temperature of −5° to 0° being maintained during the addition. The reaction mixture is then warmed to 55° and stirred for a further 15 hours at this temperature. The reaction mixture is then cooled to 0° and poured into a solution of 680 g of ammonium chloride in 2,000 ml of ice-water, with stirring. The organic phase is separated off and the aqueous phase is extracted with toluene. The combined organic solutions are washed with water, dried over sodium sulfate and evaporated in vacuo. 8-Bromo-10,11-dimethyl-dihydrodibenz[b,f]oxepin-10-ol, in the form of an oil, remains as the residue.

319 g (1 mol) of 8-bromo-10,11-dimethyl-dihydrodibenz[b,f]oxepin-10-ol (crude product) and 1.5 g of p-toluenesulfonic acid are heated in a distillation apparatus under 11 mm Hg for 1 hour at an external temperature of 180° and for 5 hours at an external temperature of 200°, water being eliminated. The distillation receiver is then changed and the 2-bromo-10,11-dimethyl-dibenz[b,f]oxepine formed is then distilled under a high vacuum; boiling point 142°–148°/0.01 mm Hg. The pale yellow distillate is dissolved in 300 ml of acetonitrile and the solution is cooled to 0°, whereupon the product crystallises out; melting point 117°–119°.

30.1 g (0.1 mol) of 2-bromo-10,11-dimethyl-dibenz[b,f]oxepine, 10.7 g (0.12 mol) of copper-I cyanide and 15 ml of dimethylformamide are heated at a bath temperature of 200° for 3 hours, with stirring. The reaction mixture is then cooled to 40° and stirred vigorously for 2 hours with 200 ml of a 50% aqueous solution of ethylenediamine and 200 ml of methylene chloride. The organic phase is then separated off and the aqueous phase is extracted twice more with 100 ml of methylene chloride. The combined organic solutions are washed with water, dried over sodium sulfate and evaporated. The residue, i.e. 2-cyano-10,11-dimethyl-dibenz[b,f]oxepine is recrystallised from hexane and melts at 112°–114°.

24.7 g (0.1 mol) of 2-cyano-10,11-dimethyl-dibenz[b,f]oxepine are dissolved in 525 ml of carbon tetrachloride and 35.6 g (0.2 mol) of N-bromosuccinimide are added to this solution. The mixture is heated to the boil, under exposure to a UV lamp, with stirring, in a nitrogen atmosphere. The mixture is kept at the boil until all the N-bromosuccinimide, which is on the base of the vessel, has been converted to succinimide floating on the solution; time taken about 5 minutes. The reaction mixture is then cooled to 20° and the succinimide is separated off by filtration. The filtrate is washed with water, dried over sodium sulate and concentrated in vacuo. On cooling, 2-cyano-10,11-bis-bromomethyl-dibenz[b,f]oxepine with a melting point of 176°–178° crystallises out.

EXAMPLE 4

12.2 g (0.075 mol) of octanoyl chloride are added dropwise in the course of 15 minutes, with stirring, to a solution of 16.7 g (0.05 mol) of 5-cyano-1,3-dihydro-2H-dibenzo[2,3:6,7]thiepino[4,5-c]pyrrole-2-propanol (prepared according to Example 2d) in 50 ml of absolute pyridine, the temperature being kept between 0° and 5°. The mixture is then stirred for a further 20 hours at room temperature. The reaction mixture is then poured into ice-water and extracted with ether. The organic phase is separated off, washed with water and, after drying over sodium sulfate, evaporated. The oily residue, i.e. 2-(3-octanoyloxypropyl)-5-cyano-2,3-dihydro-1H-dibenzo[2,3:6,7]thiepino[4,5-c]pyrrole, is heated under a high vacuum at 90°/0.01 mm Hg to constant weight.

21.4 g of the crude base are dissolved in 150 ml of acetone and a solution of 4.2 g (0.047 mol) of anhydrous oxalic acid in 22 ml of absolute ethanol is added, whereupon 2-(3-octanoyloxypropyl)-5-cyano-2,3-dihydro-1H-dibenzo[2,3:6,7]thiepino[4,5-c]pyrrole oxalate crystallises out; after recrystallisation from absolute ethanol, this melts at 188°–189°.

EXAMPLE 5

The following compound can be prepared analogously to Example 4, using the corresponding starting materials:

2-(3-Acetoxypropyl)-5-cyano-2,3-dihydro-1H-dibenzo[2,3:6,7]thiepino[4,5-c]pyrrole, melting point 101°–105° (from acetonitrile); hydrochloride melting point 180°–183° with decomposition (from absolute ethanol), from 16.7 g (0.05 mol) of 5-cyano-1,3-dihydro-2H-dibenzo[2,3:6,7]thiepino[4,5-c]pyrrole-2-propanol in 50 ml of absolute pyridine and 5.9 g (0.075 mol) of acetyl chloride.

EXAMPLE 6

A mixture of 19.7 g (0.05 mol) of 5-bromo-2(cyclopentylmethyl)-2,3-dihydro-1H-dibenzo[2,3:6,7]-thiepino[4,5-c]pyrrole and 10.7 g (0.12 mol) of copper-I cyanide in 20 ml of dimethylformamide is heated at 180° for 22 hours in a nitrogen atmosphere, with stirring. It is then cooled to 30° and diluted with 100 ml of methylene chloride and 50 ml of a 50% aqueous solution of ethylenediamine are added. The organic phase is then separated off, washed with water and, after drying over sodium sulfate, evaporated. The crystalline residue, i.e. 5-cyano-2-(cyclopentylmethyl)-2,3-dihydro-1H-dibenzo[2,3:6,7]thiepino[4,5-c]pyrrole, melts at 97°–100° after recrystallisation from acetonitrile.

In order to convert the product to the methanesulfonate, 10 g (0.03 mol) of the base are dissolved in 50 ml of acetone and 2.88 g (0.03 mol) of methanesulfonic acid are added to this solution, with stirring, whereupon 5-cyano-2-(cyclopentylmethyl)-2,3-dihydro-1H-dibenzo[2,3:6,7]thiepino[4,5-c]pyrrole methanesulfonate with a melting point of 162°–168° crystallises out.

The starting material can be prepared as follows: 47.5 g (0.1 mol) of 2-bromo-10,11-bis-bromomethyldibenzo[b,f]thiepine are dissolved in 250 ml of absolute benzene and this solution is added dropwise in the course of one hour, at 40°, to a solution of 49.5 g (0.5 mol) of (aminomethyl)-cyclopentane in 500 ml of methanol. The reaction mixture is stirred for a further two hours at 50° and the solvent is then distilled off. Water is added to the residue and the resulting suspension is extracted with ether. The organic phase is separated off, washed with water, dried over potassium carbonate and concentrated. On cooling, 2-(cyclopentylmethyl)-5-bromo-2,3-dihydro-1H-dibenzo[2,3:6,7]thiepino[4,5-c]pyrrole crystallises out.

EXAMPLE 7

Tablets containing 0.002 g of the methanesulfonate of 2-methyl-5-cyano-2,3-dihydro-1H-dibenzo[2,3:6,7]-thiepino[4,5-c]pyrrole are prepared as follows:

Composition (for 10,000 tablets)

Methanesulfonate of 2-methyl-5-cyano-2,3-dihydro-1H-dibenzo[2,3:6,7]thiepino[4,5-c]pyrrole: 20.00 g
Lactose: 250.80 g
Potato starch: 434.70 g
Stearic acid: 10.00 g
Talc: 250.00 g
Magnesium stearate: 2.50 g
Colloidal silica: 32.00 g
Ethanol: q.s.

A mixture of the methanesulfonate of 2-methyl-5-cyano-2,3-dihydro-1H-dibenzo[2,3:6,7]thiepino[4,5-c]pyrrole, the lactose and 194.70 g of potato starch is moistened with an ethanolic solution of the stearic acid and granulated through a sieve. After drying, the remainder of the potato starch, the talc, the magnesium stearate and the colloidal silica are mixed in and the mixture is compressed to tablets which each weigh 0.1 g and, if desired, can be provided with breaking notches for finer adjustment of the dosage.

EXAMPLE 8

Sugar-coated tablets containing 0.0005 g of the methanesulfonate of 2-ethyl-5-cyano-2,3-dihydro-1H-dibenzo[2,3:6,7]thiepino[4,5-c]pyrrole are prepared as follows:

Composition (for 10,000 sugar-coated tablets)

Methanesulfonate of 2-ethyl-5-cyano-2,3-dihydro-1H-dibenzo[2,3:6,7]thiepino[4,5-c]pyrrole: 5.00 g
Lactose: 180.00 g
Stearic acid: 10.00 g
Colloidal silica: 60.00 g
Talc: 180.00 g
Potato starch: 20.00 g
Magnesium stearate: 2.50 g
Sucrose (crystalline): 524.78 g
Shellack: 6.00 g
Gum arabic: 10.00 g
Dye: 0.22 g
Titanium dioxide: 1.50 g
Ethanol: q.s.

Granules are prepared from the 2-ethyl-5-cyano-2,3-dihydro-1H-dibenzo[2,3:6,7]thiepino[4,5-c]pyrrole methanesulfonate, the lactose and an ethanolic solution of the stearic acid and, after drying, these granules are mixed with the colloidal silica, the talc, the potato starch and the magnesium stearate and the mixture is compressed to sugar-coated tablet cores. These are then coated with a concentrated syrup of the sucrose, the shellack, the gum arabic, the dye and the titanium dioxide and dried. Sugar-coated tablets each weighing 0.100 g are thus obtained.

EXAMPLE 9

Capsules containing 0.002 g of the methanesulfonate of 2-(cyclopentylmethyl)-5-cyano-2,3-dihydro-1H-dibenzo[2,3:6,7]thiepino[4,5-c]pyrrole are prepared as follows:

Composition (for 1,000 capsules)

Methanesulfonate of 2-(cyclopentylmethyl)-5-cyano-2,3-dihydro-1H-dibenzo[2,3:6,7]thiepino[4,5-c]pyrrole: 2.0 g
Lactose: 253.0 g
Gelatin: 2.0 g
Maize starch: 10.0 g
Talc: 15.0 g
Water: q.s.

The methanesulfonate of 2-(cyclopentylmethyl)-5-cyano-2,3-dihydro-1H-dibenzo[2,3:6,7]thiepino[4,5-c]pyrrole is mixed with the lactose and the mixture is uniformly moistened with an aqueous solution of the gelatin and granulated through a suitable sieve (for example a sieve with an internal mesh width of 1.2–1.5 mm). The granules are mixed with the dried maize starch and the talc and the mixture is filled uniformly into the hard gelatin capsules (size 1).

EXAMPLE 10

An aqueous injection solution containing 0.001 g/ml of the methanesulfonate of 2-(cyclopentylmethyl)-5-cyano-2,3-dihydro-1H-dibenzo[2,3:6,7]thiepino[4,5-c]pyrrole is prepared as follows:

Composition (for 1,000 ampoules)

Methanesulfonate of 2-(cyclopentylmethyl)-5-cyano-2,3-dihydro-1H-dibenzo[2,3:6,7]thiepino[4,5-c]pyrrole: 1.00 g Water: q.s.

A solution of the methanesulfonate of 2-(cyclopentylmethyl)-5-cyano-2,3-dihydro-1H-dibenzo[2,3:6,7]-thiepino[4,5-c]pyrrole in 1.000 ml of water is filled into ampoules and sterilised. An ampoule contains a 0.1% solution of the active ingredient.

What is claimed is:

1. An azatetracyclic carbonitrile of the formula I

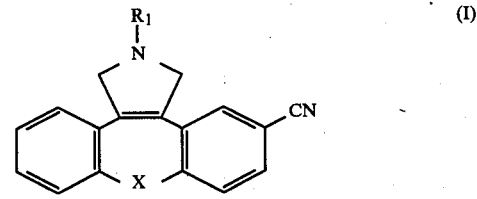

wherein $R_1$ is hydrogen, lower alkyl having 1–7 carbon atoms, cycloalkyl-lower alkyl having 4–8 carbon atoms, lower alkenyl having 3–4 carbon atoms, hydroxy-lower alkyl having 2–8 carbon atoms and the hydroxy group is separated from the ring nitrogen atom by at least two carbon atoms, lower alkoxy-lower alkyl having 3–10 carbon atoms or alkanoyloxy-lower alkyl having 3–21 carbon atoms and in the lower alkoxy-lower alkyl and alkanoyloxylower alkyl radicals the oxygen atom is separated from the ring nitrogen by at least two carbon atoms, and X is epoxy, epithio, or

 (Ia)

in which $R_2$ is hydrogen or lower alkyl having not more than 4 carbon atoms, or a pharmaceutically acceptable salt thereof.

2. A compound of the formula I indicated in claim 1, in which $R_1$ is hydrogen, lower alkyl, cycloalkyl-lower alkyl having 4–8 carbon atoms, lower alkenyl, hydroxy-lower alkyl, lower alkoxy-lower alkyl or alkanoyloxy-lower alkyl and X is epoxy or epithio, or a pharmaceutically acceptable salt thereof.

3. A compound of the formula I indicated in claim 1, in which $R_1$ is hydrogen, lower alkyl, cycloalkyl-lower alkyl having 4–8 carbon atoms, lower alkenyl or hydroxy-lower alkyl and X is epoxy or epithio, or a pharmaceutically acceptable salt thereof.

4. A compound of the formula I indicated in claim 1, in which $R_1$ is hydrogen, methyl, ethyl, propyl, cyclopentylmethyl or 3-hydroxypropyl and X is epoxy or epithio, or a pharmaceutically acceptable salt thereof.

5. A compound according to claim 1 which is 2-Methyl-5-cyano-2,3-dihydro-1H-dibenzo[2,3:6,7]-thiepino[4,5-c]pyrrole or a pharmaceutically acceptable salt thereof.

6. A compound according to claim 1 which is 2-(Cyclopentylmethyl)-5-cyano-2,3-dihydro-1H-dibenzo[2,3:6,7]thiepino[4,5-c]pyrrole or a pharmaceutically acceptable salt thereof.

7. A compound according to claim 1 which is 5-Cyano-1,3-dihydro-2H-dibenzo[2,3:6,7]thiepino[4,5-c]pyrrole-2-propanol or a pharmaceutically acceptable salt thereof.

8. A pharmaceutical composition useful in the treatment of states of agitation in a warm-blooded animal comprising a therapeutically effective amount of a compound according to claim 1 or a pharmaceutically acceptable acid addition salt thereof and a pharmaceutical carrier.

9. A pharmaceutical composition according to claim 8, which contains 2-Methyl-5-cyano-2,3-dihydro-1H-dibenzo[2,3:6,7]thiepino[4,5-c]pyrrole or a pharmaceutically acceptable salt thereof.

10. A pharmaceutical composition according to claim 8, which contains 2-(Cyclopentylmethyl)-5-cyano-2,3-dihydro-1H-dibenzo[2,3:6,7]thiepino[4,5-c]pyrrole or a pharmaceutically acceptable salt thereof.

11. A pharmaceutical composition according to claim 8, which contains 5-Cyano-1,3-dihydro-2H-dibenzo[2,3:6,7]thiepino[4,5-c]pyrrole-2-propanol or a pharmaceutically acceptable salt thereof.

12. A method of treating states of agitation in a warm-blooded animal which comprises administering to said animal a therapeutically effective amount of a compound according to claim 1, or a pharmaceutically acceptable acid addition salt thereof.

13. A method according to claim 12, which comprises administering a therapeutically effective amount of 2-Methyl-5-cyano-2,3-dihydro-1H-dibenzo[2,3:6,7]-thiepino[4,5c]pyrrole or a pharmaceutically acceptable salt thereof.

14. A method according to claim 12, which comprises administering a therapeutically effective amount of 2-(Cyclopentylmethyl)-5-cyano-2,3-dihydro-1H-dibenzo[2,3:6,7]thiepino[4,5-c]pyrrole or a pharmaceutically acceptable salt thereof.

15. A method according to claim 12, which comprises administering a therapeutically effective amount of 5-Cyano-1,3-dihydro-2H-dibenzo[2,3:6,7]thiepino[4,5-c]pyrrole-2-propanol or a pharmaceutically acceptable salt thereof.

* * * * *